United States Patent [19]

Massof et al.

[11] Patent Number: 4,634,243

[45] Date of Patent: Jan. 6, 1987

[54] GLAUCOMA DETECTION UTILIZING PATTERN DISCRIMINATION TEST

[75] Inventors: Robert W. Massof, Baltimore; John N. Mangat-Rai, Gaithersburg, both of Md.

[73] Assignees: LKC Systems, Inc., Gaithersburg; Vision Research Associates, Inc., Baltimore, both of Md.

[21] Appl. No.: 686,879

[22] Filed: Dec. 26, 1984

[51] Int. Cl.⁴ .............................................. A61B 3/02
[52] U.S. Cl. ................................... 351/243; 351/224; 351/246
[58] Field of Search ............... 351/224, 225, 226, 239, 351/243, 246

[56] References Cited

U.S. PATENT DOCUMENTS

| | | |
|---|---|---|
| Re. 28,921 | 8/1976 | Haines et al. |
| 3,718,386 | 2/1973 | Lynn et al. |
| 3,883,234 | 5/1975 | Lynn et al. |
| 3,883,235 | 5/1975 | Lynn et al. |
| 3,982,828 | 9/1976 | Woolf |
| 4,045,130 | 8/1977 | Krahn |
| 4,063,807 | 12/1977 | Gelius et al. |
| 4,260,227 | 4/1981 | Munnerlyn et al. |
| 4,346,968 | 8/1982 | Melin et al. |
| 4,392,725 | 7/1983 | Sheingorn |

OTHER PUBLICATIONS

Van de Grind, W. A., "Detection of Coherent Movement in Peripherally Viewed Random-dot Patterns", Journal Opt. Soc. Am., vol. 73, No. 12, p. 1674, (Dec., 1983).

Primary Examiner—Rodney B. Bovernick
Attorney, Agent, or Firm—Pollock, VandeSande & Priddy

[57] ABSTRACT

The present invention psychophysically detects earliest signs of loss of vision due to nerve loss in glaucoma and ocular hypertension. An instrument employs a dynamic random dot background field and a movable target that consists of a circular area in which the dots are spatially and temporally coherent. Thus, visual fields will be based on pattern discrimination rather than on conventional measures of luminance discrimination.

14 Claims, 9 Drawing Figures

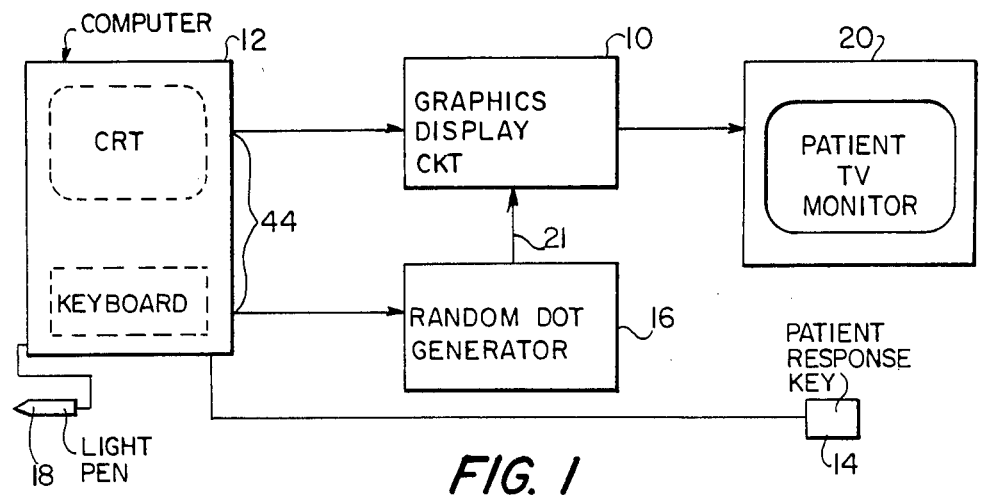
FIG. 1
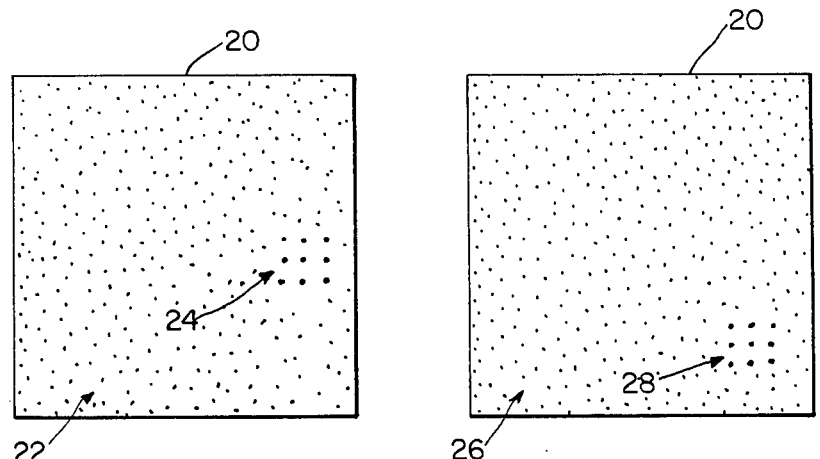
FIG. 2A
FIG. 2B
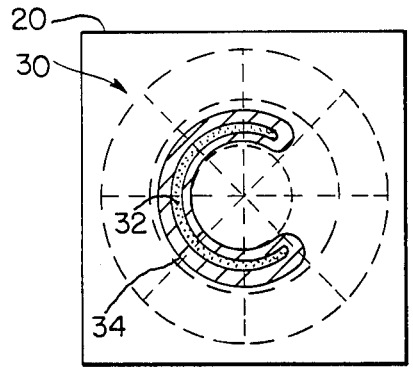
FIG. 3

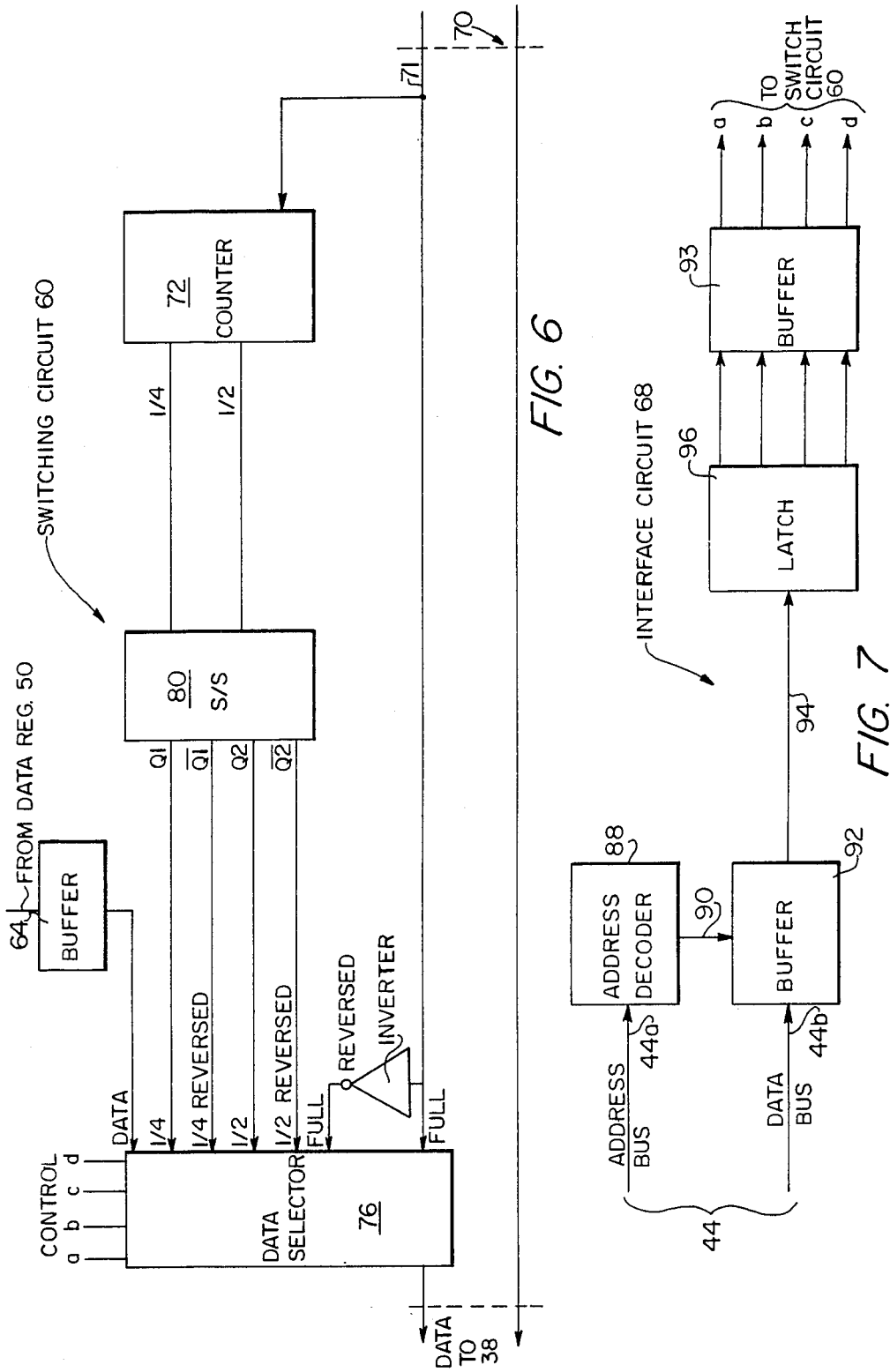

GLAUCOMA DETECTION UTILIZING PATTERN DISCRIMINATION TEST

BACKGROUND OF THE INVENTION

The following invention relates to pattern discrimination test system for early glaucoma detection, and more particularly to a video system which displays to a subject a movable coherent dot pattern within a background of randomly changing dots.

Psychophysical testing in primary open angle glaucoma has three primary functions: (1) to characterize any loss of visual function which has occurred; (2) to provide a basis for predicting the future course of the untreated disease; and (3) to monitor the effects of treatment.

Psychophysical evaluation of the visual field has long been the method used for the clinical diagnosis of glaucoma. Presently, such evaluation is largely limited to the measurement of increment thresholds for small circular achromatic stimuli (e.g., conventional kinetic and static perimetry). The earliest signs of glaucoma found by such tests may include: vertical enlargement of a blind spot; small 37 wedge-shaped" scotomas in the area surrounding the macula; small nasal steps (sensitivity differences between the upper and lower nasal field); increased variability of sensitivity at some visual field locations. These defects may later expand to become "Bjerrum scotomas," which arc from the blind spot around the macula to the horizontal nasal meridian. Bjerrum scotomas often appear simultaneously in the upper and lower field, but the upper and lower defects are rarely, if ever, symmetrical. The fovea is usually spared until late in the disease, and patients with a nearly total loss of visual field may retain essentially normal foveal sensitivity and acuity.

It has been shown recently that conventional kinetic and static visual fields testing do not provide a full indication of loss of optic nerve fibers which is the generally agreed-upon cause of loss of visual function.

The loss of optic nerve fibers can be seen indirectly in abnormal cupping of the optic disk and directly in histologic studies of glaucomatous eyes. Fiber loss can also be observed directly in the retinal nerve fiber layer by photographing the fundus in red-free light.

Using a variety of techniques, prior art investigators have now convincingly shown that the visual field can sometimes appear normal even after substantial fiber loss. Field defects revealed by conventional perimetry may thus be a much less sensitive indicator of glaucomatous nerve damage than was previously suspected.

The pattern of fiber loss in glaucoma is not yet completely understood. Complicating factors include the fact that strict retinotopic correspondence is not maintained in a single fiber bundle. Therefore, a strictly focal pattern of fiber loss does not imply a corresponding pattern of sharply defined, localized scotomas.

BRIEF DESCRIPTION OF THE PRESENT INVENTION

We are led by these facts to consider an alternative form of visual fields testing which will be sensitive to a breakdown of the intergrative properties of retina and potentially signal the loss of smaller numbers of optic nerve fibers in a localized region than is possible with conventional perimetric techniques. This test is based on the principle that the loss of a relatively small percentage of ganglion cells might be enough to significantly distort the cortical retinotopic map. For example, if a given small stimulus would normally be detected by a dozen ganglion cells in its neighborhood, the loss of only two or three strategically placed cells would be enough to shift the "center-of-gravity" of the remaining net response.

We propose to construct stimuli for which the precise coding of relative position is the only basis for detection. An example is a small patch of evenly spaced dots surrounded by a larger field of identical randomly spaced dots of the same average density. "Pattern thresholds" to this stimulus can be measured by gradually randomizing the target dot positions until the pattern disappears. Local distortions in the apparent relative positions of the target dots due to ganglion cell loss would introduce additional randomization and raise the pattern threshold.

This is based on the following argument: Retinal ganglion cell receptive fields span visual angles up to several degrees when the antagonistic surrounds are included, and lateral interactions can be demonstrated over even greater distances under certain conditions. Also, neighboring ganglion cell receptive fields overlap each other substantially, so that each retinal location is covered by a number of different ganglion cell receptive fields. If we make the reasonable assumption that the effective retinal position of each ganglion cell is coded by the center of its receptive field, it follows that each stimulus point produces ganglion cell responses over a relatively large region of the visual field. It is thus perhaps understandable that a large percentage of the ganglion cells in a particular region must be lost in order to produce significant sensitivity losses to small single targets.

As we have described it, pattern discrimination perimetry may be expected to show psychophysical deficits in visual function at an earlier stage in disease progression than detected by standard perimetry. A number of other psychophysical testing modes have shown similar sensitivity to early functional loss although the mechanisms of loss may be different for the different modes. Some of the specific deficits observed include (1) blue-yellow acquired color vision defects; (2) reduced flicker sensitivity; (3) reduced contrast sensitivity to sinusoidal gratings; (4) delay of dark-adaptation and reduced dark adapted sensitivity; and (5) loss of lateral inhibition. Interestingly, the locations of these deficits tend to be poorly correlated with conventional field defects and are sometimes found even in "ocular hypertensives" who show no conventional field defects at all. It is not yet clear, however, whether such changes are precursors to conventional scotomas, global responses to high intraocular pressure that are unrelated to specific nerve damage, or even (in some cases) misinterpretations of normal visual changes due to aging.

Further support for the use of a pattern stimulus in a perimetric type of test comes from other recent investigations of pattern perception. These studies have shown that the visual system can be quite sensitive to both static differences and temporal changes of the relative positions of local pattern elements when the spatial frequency amplitude spectrum is held constant. To our knowledge, however, no one has yet applied these findings to the clinical investigation of the visual field. To this end the present invention utilizes a novel ophthalmic stimulator which is a device that displays to the subject a coherent dot pattern within a background of random dots. The random dots, however, have the same density as the coherent pattern.

The invention is also believed to be useful in testing for other classes of retinal diseases as well as neuro-ophthalmic disorders.

The above-mentioned objects and advantages of the present invention, will be more clearly understood when considered in conjunction with the accompanying drawings, in which:

BRIEF DESCRIPTION OF THE FIGURES

FIG. 1 is a block diagram of the basic system of the invention.

FIG. 2A is a pattern discrimination display generated by the system of the present invention.

FIG. 2B is a view similar to that of FIG. 2A but with a fixed pattern displaced relative to that shown in FIG. 2A.

FIG. 3 is a pictoral representation of test results as effected by the system of the present invention.

FIG. 6 is a block diagram of a switching circuit as employed in the selector circuit of FIG. 5.

FIG. 7 is a block diagram of an interface circuit employed in the selector circuit of the present invention.

DETAILED DESCRIPTION OF THE INVENTION

Figure 4:
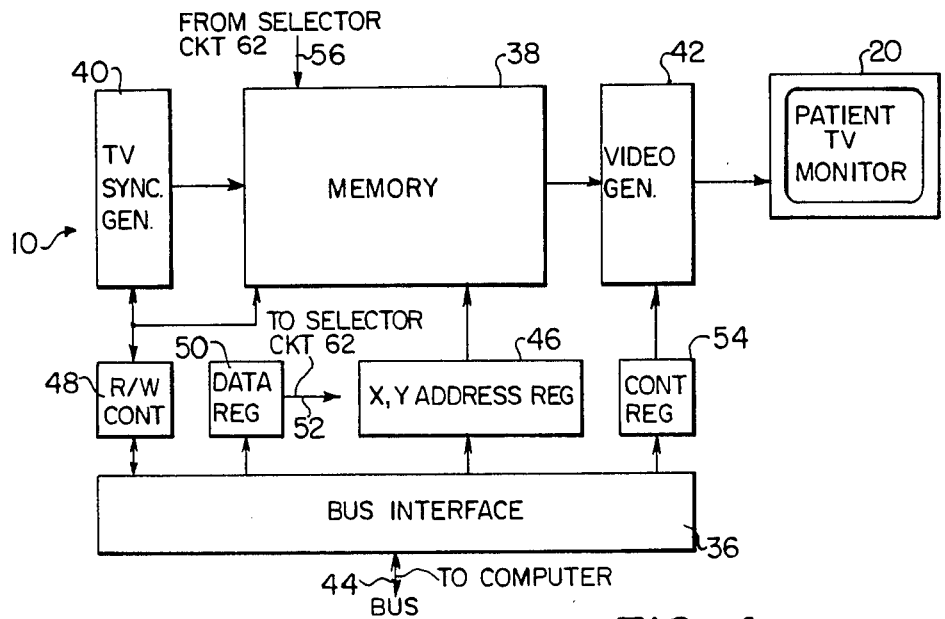
FIG. 4 is a block diagram of a graphics display circuit as utilized in the present invention.

FIG. 1 represents a basic block diagram of the present invention. A graphics display circuit 10 has a memory location for each pixel and can be read from or written into by a computer 12. Each pixel represents a point on a pattern used in the detection of glaucoma. The pattern is displayed on a conventional TV monitor 20. The graphics display circuit 10 may be of the type manufactured by Matrox Electronics Systems, Limited of Canada and identified as graphics display board ALT-512. The computer 12 may be of the type manufactured by North Star, Inc. As will be described in greater detail hereafter, the eye test pattern is comprised of a random dot pattern which is constantly changing upon which is superposed a fixed dot patch pattern movable under the control of an operator. The random dots are generated by the conventional random dot generator 16 connected to the graphics display circuit 10 through a connecting cable 21.

FIG. 2A illustrates a typical display during a testing operation in accordance with the present invention. A first random dot pattern is generally indicated by reference numeral 22. Within the random dot pattern is superposed a fixed dot pattern or patch generally indicated by reference numeral 24. In FIG. 2A this fixed dot pattern is indicated as a three-by-three matrix. However, as should be understood, other fixed dot patterns are equally applicable for the present invention.

FIG. 2B illustrates a changed random dot pattern 26 and the three-by-three matrix has moved to another location indicated by reference numeral 28. As previously indicated in the Brief Description of the Invention, an individual who has experienced nerve damage as a result of glaucoma or pre-glaucoma conditions will be unable to detect the fixed pattern as it is moved through certain critical areas in a patient's field of view. In order to obtain maximum benefit from the random dot and fixed patterns, in a preferred embodiment of the invention, the video display 20 is of the giant TV screen type as opposed to smaller conventional CRT monitors.

FIG. 3 illustrates the result of a testing procedure. The polar coordinate axes generally indicated by 30 represents a field of view of a patient undergoing testing. The generally "C" plot or trace indicates the area where a patient undergoing testing was unable, or has difficulty, discerning the fixed dot patterns in FIGS. 2A and 2B. The solid area 32 represents those areas in the field of view where the fixed pattern could not be discerned, indicating substantial degeneration, while the cross-hatched area 34 indicates some degeneration of nerve tissue.

In actual operation, the patient would be viewing monitor 20 at a distance of one meter. The operator would be seated at computer 12 controlling the display parameters and position via the keyboard or light pen 18. The patient presses the key 14 upon seeing the pattern. This marks the computer's CRT. A printer (not shown) may produce a printout of the screen showing the patient's visual field superimposed on the polar axes 30.

The computer software is designed to present to the patient a visual field stimulus consisting of a regular dot pattern embedded in a random dot background. The size of the dot pattern, the dot density, and the coherence of the dots (i.e., degree of randomness of the dot placement) can be manipulated by the operator. The software displays polar axes for the operator and moves a cursor over the polar axes. The location of the cursor on the axes corresponds to the location of the dot pattern in the patient's visual field. The operator can choose to perform kinetic or static visual field measures. Pre-programmed automatic visual field measures can be made, or the operator can measure visual fields manually by using light pen 18. In the latter case, the operator simply positions the light pen on the polar axes, presses a switch on the light pen, and the target and cursor are automatically repositioned to the light pen coordinates. By holding the switch down, the target can be moved smoothly and continuously with the light pen. The patient is provided with a response key 14. For kinetic perimetry, the software generates a mark on the polar axes when the response key is depressed. These marks are then connected with vectors to create isopters. For static perimetry, the software detects the response key depression and records a positive response for target detection. In the case of kinetic perimetry, the target density, size and coherence are held constant for each isopter. In the case of static perimetry, either target coherence or dot density or size can be manipulated to measure detection threshold at each visual field location.

FIG. 4 illustrates in detail the graphics display circuit 10 previously indicated in FIG. 1. The circuit includes a refresh memory 38 connected to a TV sync generator 40 and a video generator 42. A bus interface 36 is interposed between a bus 44 connected to the computer 12' (FIG. 1) and a series of controls and registers including XY address registers 46 which permits the addressing of each display dot (pixel), the circuit having the capability of either being written into or read out from memory 38. The control register 54 is connected between the bus interface 36 and the video generator 42.

In order to permit the fixed dot pattern to be within the larger random dot pattern, the data register 50 has been modified from its typical configuration so that it receives fixed pattern data via bus interface 36 and a transfer of this data to memory 38 is controlled by a selector circuit 62 to be discussed in connection with FIG. 5. As will be seen from FIG. 4, the selector circuit provides the fixed pattern data to the memory 38 via input lead 56.

Figure 5:
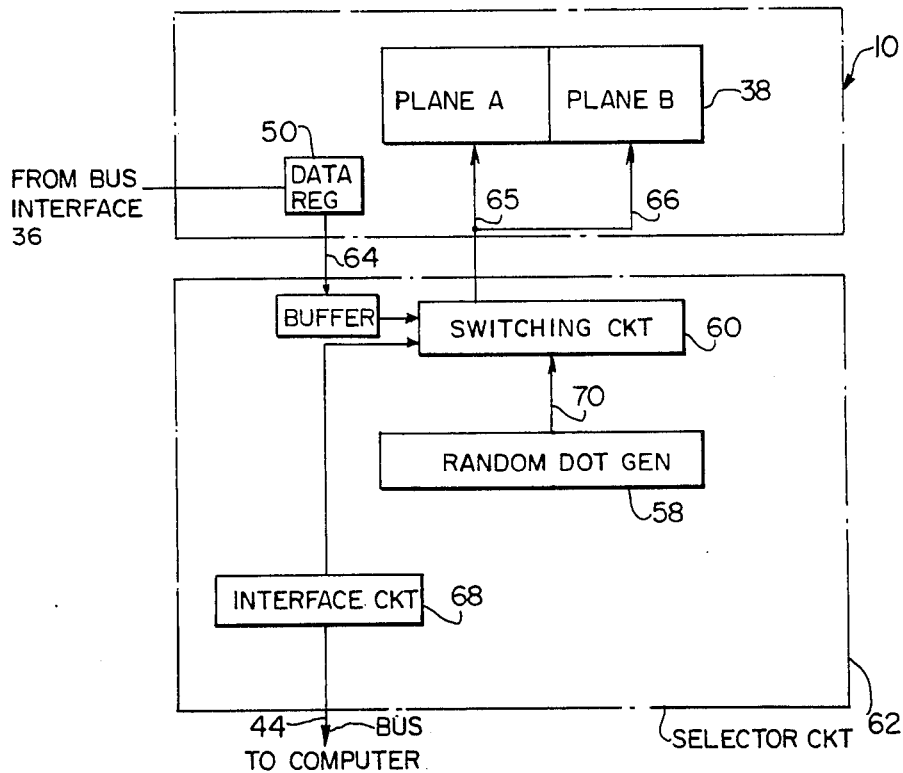
FIG. 5 is a block diagram of a selector circuit which communicates with the memory of a graphics display circuit for displaying a fixed pattern in a random dot pattern background field.

FIG. 5 shows the selector circuit 62 in greater detail. The figure also indicates in greater detail that the memory 38 of the graphics display circuit 10 is preferably divided into multiple memory planes such as plane A and plane B, each representing different "pages" of time-varying displays for patient testing. Thus, at a particular moment of time, random dot generator 58 outputs a random dot pattern to plane A of the graphics display memory via switching circuit 60 and connecting line 65. This occurs after the computer software generates a "clear" command which causes random dots to be written into the memory locations of plane A. The previously described fixed pattern data is sent to data register 50 from the bus interface 36 (FIG. 4). After a single page of random dots has been written into plane A, the fixed dot pattern, for example the nine dot matrix, overrides those pixels of the random dot pattern which are coincident herewith. Accordingly, a display may indicate the gear composite pattern shown in FIG. 2A. While this composite pattern is displayed, the selector circuit 62 operates to write in a page of composite pattern data into plane B. Accordingly, after a subsequent "clear" command, a different random dot pattern, generated by random dot generator 58, is written into plane B, via switching circuit 60 and connecting lead 65. The pixel information for a newly located fixed pattern can then be read into data register 50, as previously done, so that the composite pattern now resembles that shown in FIG. 2B.

The interface circuit 68 is connected between bus 44 and switching circuit 60 and controls the appearance of the various pixels in terms of density, as well as the color which the pixels will present when displayed.

FIG. 6 illustrates in detail the switching circuit 60 previously discussed in connection with FIG. 5. Reference numeral 70 generally indicates a plurality of data lines connecting the output of the random dot generator 58 (FIG. 5) to the input of the switching circuit 60. In FIG. 6 only a single channel is shown for switching a first random line 71. However, it is to be understood that a plurality of similarly illustrated channels are duplicated to handle each corresponding bit of the random dot generator signal. The input of counter 72 is connected to random line 71 and a plurality of counter outputs serve to select pixel density. Counter 75 is a two-stage binary counter, with the output of the first stage feeding the second stage. Both stages divide by two. Thus, the output of the first stage is the one-half density line (which also feeds the input to the second stage); and the output of the second stage is the one-quarter density line. Control input lines a, b, c and d are generated by the interface circuit 68 (FIG. 5). These line respectively cause full density, half density or quarter density with regard to display pixels. The interface circuit 68 (FIG. 5) generates the signal on the control lines a-d in accordance with data it receives from the computer, along bus 44 (FIG. 4). The particular structure of the interface circuit is to be discussed in connection with FIG. 7. The output from counter 72 is connected to a single shot 80. The outputs $Q_1$ and $Q_2$ of the single shot 80 have random pixels to be displayed which will be black on a white background, while the output lines $\overline{Q}_1$ and $\overline{Q}_2$ from the single shot 80 have pixels which will be white on a black background, assuming a black and white display. The data selector 76 is connected to the output of the single shot 80 and has a first input line 64 connected from the data register 50 (FIG. 5) via a buffer. One of the other inputs to the data selector becomes active during a clear function, according to the state of the control lines.

FIG. 7 illustrates the interface circuit 68 in greater detail. A computer-generated valid address is input along address bus 44a to address decoder 88. Control pulses are then gated through the address decoder 88 to buffer 92 via a connecting line 90. The buffer 92 then accepts data appearing along the data bus portion 44b thereby allowing the data to be transferred, via connecting line 94, to latch 96. The latch has a plurality of control lines, for example the five control lines a–d for controlling the switching circuit 60 as previously discussed in connection with FIG. 5 via buffer 93.

Figure 8:
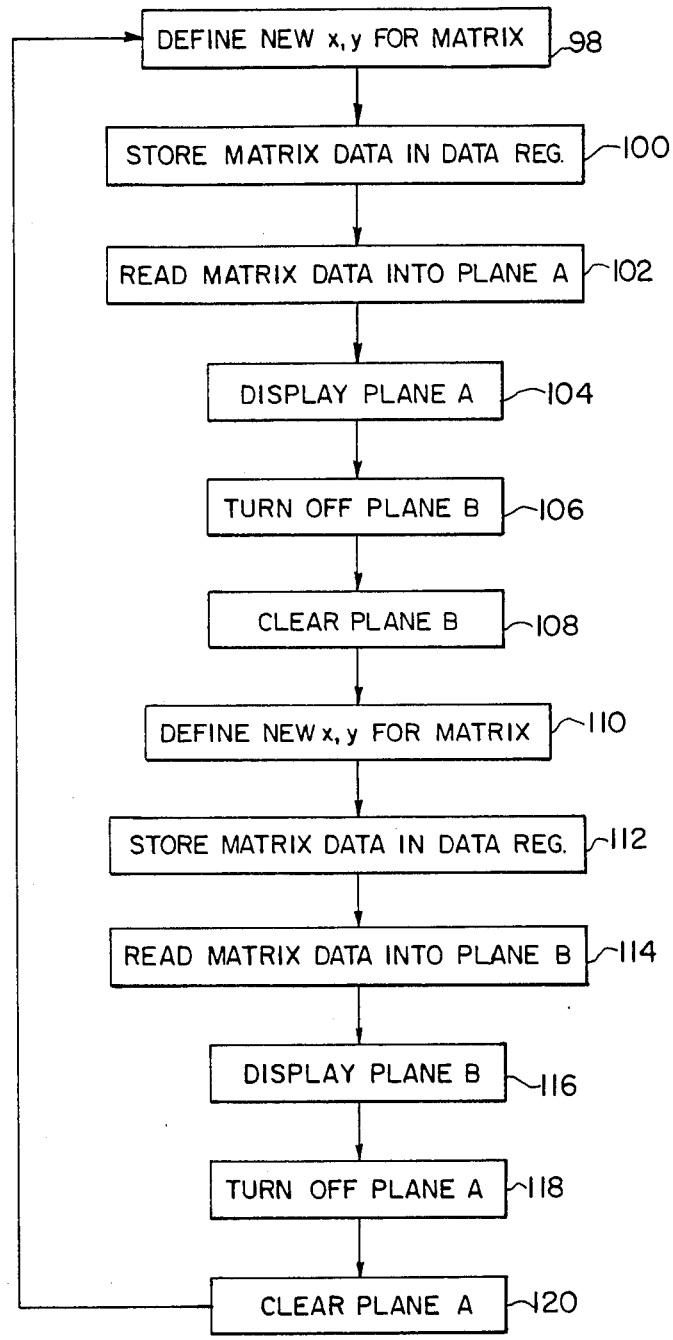
FIG. 8 is a basic flow chart of the program for generating the display of the present invention from two planes of memory.

FIG. 8 illustrates a simplified flow chart of the software which controls the operation of the present invention and the flow chart should be considered in conjunction with FIGS. 4 and 6.

A physician operating the testing system of the present invention defines a fixed pattern, such as the three x three matrix fixed pattern and the center coordinate for the matrix is defined by the operator in step 98 of the flow chart in FIG. 8. In actuality, the new coordinates are stored in the x, y address register 46 (FIG. 4).

The data concerning the pixels of the displayed fixed pattern matrix is stored in data register 50 as indicated in step 100. The next step 102 witnesses a reading of matrix data from the data register to plane A of memory 38 (FIG. 5). Thereafter, during step 104, the contents of plane A are displayed and this will enable a patient undergoing examination to view the fixed pattern matrix against a random dot background as previously discussed in connection with FIGS. 2A and 2B. While the contents of plane A are being displayed, the previously displayed contents of plane B may be cleared during step 108 so that plane B includes only random dot data. The following step 110 enables the operator to define new x, y coordinates for the matrix center as exemplified during step 110. The steps now become repetitive for the alternate planes of memory 38. Thus, the matrix data relating to the new x, y coordinates are stored in the data register during step 112. Then, during step 114, the matrix data is read into plane B and subsequently displayed during step 116. Simultaneous with the display of the data stored in plane B, the display from plane A, during step 118, is turned off. Then, during step 120 the contents of plane A are cleared thereby randomizing the contents and enabling a reiteration of the flow chart at step 98.

Although the invention has been discussed in terms of its applicability to glaucoma and ocular hypertension, it is similarly believed to have utility in testing for other retinal diseases as well as neuro-ophthalmologic disorders.

It should be understood that the invention is not limited to the exact details of construction shown and described herein for obvious modification will occur to persons skilled in the art.

We claim:

1. A method for detecting eye disease and disorders comprising the steps:

positioning a patient in front of a video display having a viewing surface corresponding to substantially the entire human field of normal vision;

generating a random dot pattern on the display;

superposing a smaller fixed pattern on the random dot pattern;

selectively moving the fixed pattern in the random dot pattern; and determining where a patient fails to discriminate the fixed pattern within the random dot pattern, wherein such failure is indicative of eye disease or disorder.

2. The method set forth in claim 1 wherein the movement of the fixed pattern along a path is in accordance with a preselected program.

3. The method set forth in claim 1 wherein the movement of the fixed pattern is manually governed by a tester.

4. The method set forth in claim 1 wherein the average graphic density of the fixed pattern is the same as that of the random dot pattern.

5. A method for detecting nerve damage to the eye comprising the steps:

(a) positioning a patient in front of a video display having a viewing surface corresponding to substantially the entire human field of normal vision;

(b) storing data corresponding to a first random dot pattern;

(c) displaying the random dot pattern;

(d) superposing a smaller fixed pattern on the displayed random dot pattern;

(e) storing data corresponding to a second random dot pattern;

(f) superposing a displaced fixed pattern on the second displayed random dot pattern;

(g) reading from storage, the data corresponding to the second random dot pattern;

(h) displaying the read out data of the second random dot pattern in lieu of the first;

(i) erasing the stored data of the first random dot pattern;

iterating (b)–(i) for third and subsequent random dot patterns thereby smoothly displaying a constantly changing random dot pattern with a selectively displaced superposed fixed pattern;

whereby a patient's failure to discriminate the fixed pattern in any area within the random dot pattern is indicative of nerve damage in a corresponding area of the retina.

6. The method set forth in claim 5 wherein the graphic average density of the fixed pattern is the same as that of the random dot pattern.

7. The method set forth in claim 6 wherein the graphic average density of the random dots and the fixed pattern are variable.

8. A system for detecting nerve damage of the eye comprising;

means for generating random dot data;

memory means connected at its input to the random dot generating means for storing the data;

means connected to the memory means for storing data corresponding to a preselected fixed pattern; and enlarged video display means connected to an output of the memory means for displaying the fixed pattern superposed on the random dot pattern;

wherein a patient undergoing testing is positioned in front of the display means so as to be presented with a display area covering a normal field of vision;

whereby an inability to discriminate the presence of the fixed pattern in the random dot pattern is indicative of nerve damage.

9. The system set forth in claim 8 wherein the memory means includes a plurality of planes to store data corresponding to multiple pages of random dot patterns resulting in the display of a fixed pattern superposed on varying random dot patterns.

10. The system set forth in claim 8 together with computer means connected to the memory means and the random dot generating means for moving the fixed pattern in a background field of the random dot pattern in accordance with a preprogrammed path.

11. The system set forth in claim 8 together with a computer terminal connected to the memory means and the random dot generating means for permitting movement of the fixed pattern under control of a system operator.

12. A system for detecting eye disease and disorder comprising:

means for generating random dot data;

memory means for storing data therein;

video display means connected to the memory for displaying the stored data and having sufficient display area to cover a normal patient's field of view when the patient is placed in front of the display means;

a data register for storing data therein representing a fixed pattern;

switching means having a first input connected to the output of the data register, and a second input connected to the output of the generating means, the output of the switching means being connected to the memory means;

and a computer connected to the switching means for controlling its continuing switching operation between the data register and the generating means whereby the fixed pattern is superposed against a time varying display of random dots;

wherein a patient's inability to differentiate the fixed pattern from the random dot display being indicative of eye disease or disorder.

13. The system set forth in claim 12 together with program means for causing the computer to generate fixed pattern data which varies its path as a function of time thereby displaying a moving fixed pattern in a time varying random dot pattern background.

14. The system set forth in claim 13 wherein the memory means includes a plurality of planes for storing random dot and fixed pattern data for respectively spaced instants of time, the data of a particular plane being displayed momentarily and then erased to permit refresh with updated random dot and fixed pattern data for subsequent display.

* * * * *